United States Patent [19]
Meyer

[11] Patent Number: 5,612,819
[45] Date of Patent: Mar. 18, 1997

[54] HOLDER FOR HIGH RESOLUTION TISSUE SAMPLE IMAGING

[76] Inventor: Robert D. Meyer, 4202 Bear Lodge Ct., Houston, Tex. 77084

[21] Appl. No.: 493,964

[22] Filed: Jun. 23, 1995

[51] Int. Cl.6 ................................................. G01N 21/01
[52] U.S. Cl. ........................................ 359/391; 356/244
[58] Field of Search .................................. 359/391–395, 359/809; 356/244

[56] References Cited

U.S. PATENT DOCUMENTS 4,501,495 2/1985 Faulkner et al. ...................... 356/244
5,325,232 6/1994 Lahcanski et al. ..................... 359/391

*Primary Examiner*—Timothy P. Callahan
*Assistant Examiner*—Eunja Shin
*Attorney, Agent, or Firm*—Bush, Riddle & Jackson

[57] ABSTRACT

A system to obtain a high resolution image of a large tissue sample for viewing by a clinician includes a rectangular holder that receives a microscope slide and which includes a glass filter that reduces the amount of illumination of the sample without reducing the Kelvin light temperature, and a scanner that receives the holder and produces electrical signals which are fed to the hard drive of a computer where a high resolution image of the tissue sample is displayed on the monitor.

10 Claims, 1 Drawing Sheet

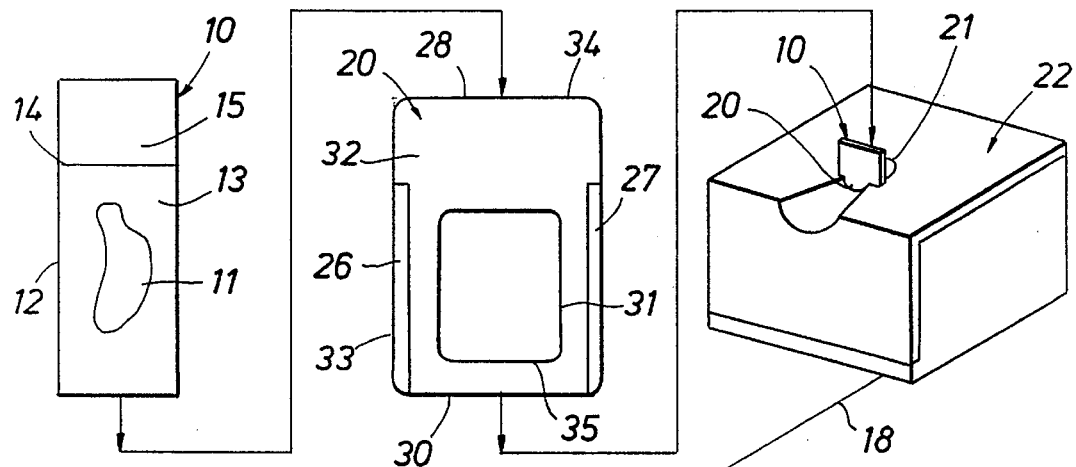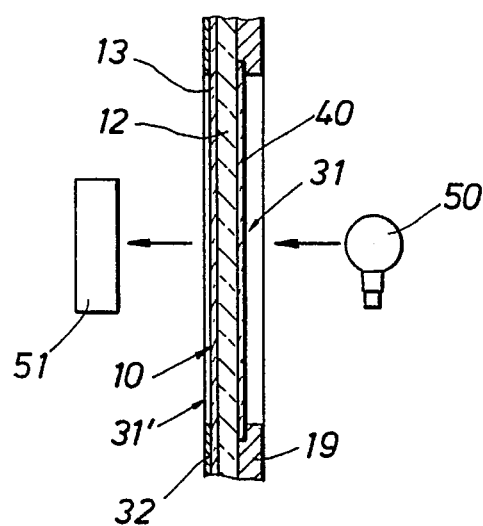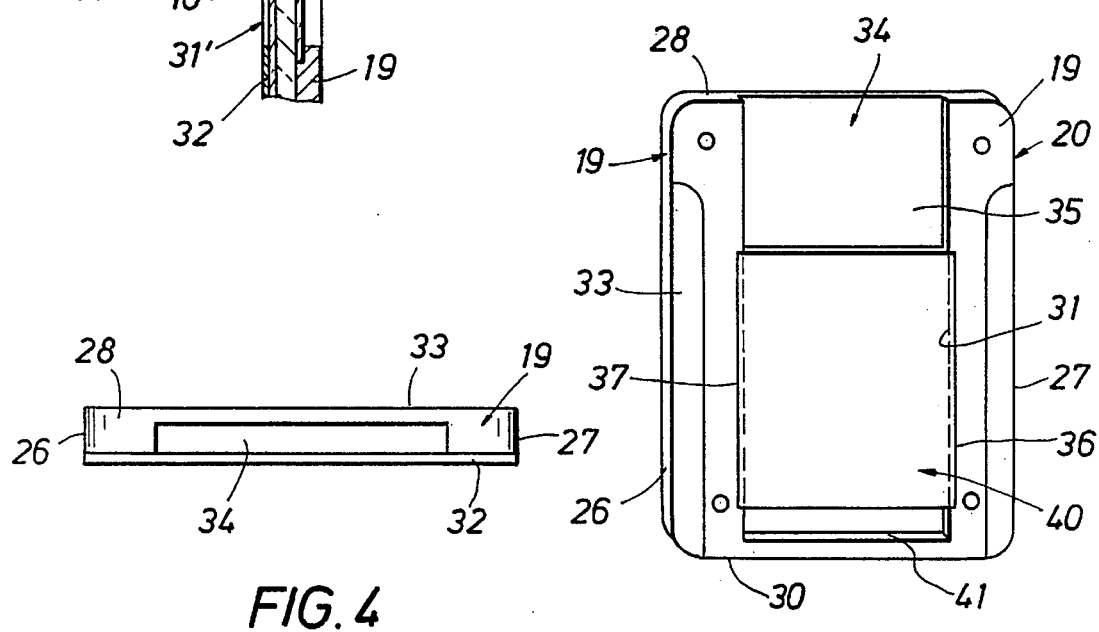

HOLDER FOR HIGH RESOLUTION TISSUE SAMPLE IMAGING

FIELD OF THE INVENTION

This invention relates generally to the imaging of samples such as those used in research work in the field of medicine, and particularly to new and improved high resolution imaging of large tissue samples mounted in slides.

BACKGROUND OF THE INVENTION

A conventional practice in this field is to attach a video camera to a microscope, in order to generate signals that are representative of an image in the field of view of the microscope. Such signals are fed to a computer having a capture card (frame grabber), and the resultant image is displayed on the monitor. The display on the monitor typically has a resolution in the order of 640 by 480 pixels, provided the resolution of the camera is equal to or greater than this value. When using modern laboratory microscope at a low power objective such as 1×, 2.5×, 4×, the field of view, which is circular, ranges from about 20 mm to 5 mm, although certain more expensive research instruments can have a field of view in the order of 28 mm to 7 mm. When a video camera is attached to the microscope the field of view decreases to about 10 mm to 2.5 mm, since the camera will have a rectangular field of view with an aspect ratio of 4 to 3. Thus the largest rectangular field of view that a typical video camera can display when attached to a microscope is about 10mm×7.5 min. This severely limits the size of the largest tissue sample image that can be viewed on a monitor to such size, namely 10mm×7.5 mm.

Moreover, a typical laboratory microscope video camera and display system is very expensive, and can cost in the range of from $10,000–$15,000 or more, excluding the cost of the microscope. To obtain larger fields of view and higher capture and display resolutions, the above-mentioned research microscopes can be used with additional intermediate lenses and higher performance capture and display electronics. However such systems cost tens of thousands of dollars more than the typical systems.

Microscope specimen slides that are viewed through a microscope usually are made of glass and commonly are rectangular having side dimensions of 1 in.×3 in. The thickness dimension is 1.1 mm. A sample of histological tissue is prepared and sliced to a very thin section (3 to 5 microns), which is mounted on the glass slide and protected by a rectangular coverslip that has dimensions of 40 mm long×20 mm wide×0.15 mm thick. The coverslip limits the size of the largest tissue sample that can be mounted. Such slides are viewed by pathologists, anatomists and biologists and the like on a daily, routine basis. Indeed literally millions of such slides are created and viewed by thousands of researchers and clinicians every day, so that improvements in accordance with this invention have wide application in the art.

As noted above, where the size of the tissue sample exceeds 10 mm×7.5 mm, the use of a microscope and video camera to capture and display an image thereof has an inherent, very serious problem. Even though the specimen slide and coverslip can accommodate a fairly large tissue sample section, for example up to 40 mm×24 mm, there is no way when using conventional technology to display the entire sample section for viewing by the clinician. Of course as a practical matter, the side dimensions of a slide do not exceed 36 mm×24 mm.

It is an object of the present invention to provide a new and improved imaging system that enables display of large tissue samples at high resolution.

Another object of the present invention is to provide a new and improved imaging system that employs a scanner and a unique slide holder that enables display of the entirety of a large tissue sample with high resolution.

Yet another object of the present invention is to provide a new and improved holder for a tissue sample slide, such holder including a glass filter having neutral density to reduce the amount of light transmitted through the slide by a predetermined amount without affecting the Kelvin temperature of such light.

SUMMARY OF THE INVENTION

These and other objects are attained in accordance with the concepts of the present invention through the provision of a unique slide holder apparatus that is dimensioned to be received in the receptacle of an electronic scanner having a charge-coupled array that can scan a slide such as a 35 mm photographic slide and provide a high resolution image thereof. The output of the scanner is fed to a computer which generates a display on a video monitor. The holder apparatus has front and rear walls that define a viewing window. A piece of filter glass is retained between the walls on the outer side of the holder apparatus, such glass being optically flat, clear, and of neutral density. The flat characteristic prevents distortion, and the glass has no discernable impurities, i.e. is clear. The neutral density characteristic means that the Kelvin temperature of light passing through it is not affected, however it is preferred that the amount of light be reduced by about 40%. A pocket is formed through one end of the holder and between the filter glass and the rear wall thereof. Such pocket has width, thickness and length dimensions such that the tissue sample slide with its coverslip can be inserted therein from such end and, when fully seated, a sufficient length of the slide remains exposed beyond the end wall of the holder apparatus to enable its insertion and withdrawal with the fingers. When positioned in the scanner receiver, the CCD array of the scanner can scan the entire slide and its large tissue sample at a high rate with extremely high resolution and provide an accurate replication of the information in the slide. The display can have a resolution as high as 2700×1800 dots per inch (dpi). The image is in color, can be of entire sections of glands and arteries and the like, and is accomplished in a quick and economical manner.

BRIEF DESCRIPTION OF THE DRAWINGS

The present invention has the above as well as other objects, features and advantages which will become more clearly apparent in connection with the following detailed description of a preferred embodiment, taken in conjunction with the appended drawings in which:

FIG. 1 is a schematic diagram of the overall imaging system of the present invention.

FIG. 2 is a fragmentary, schematic side sectional view of the holder of the present invention with slide positioned therein.

FIG. 3 is a front isometric view of the holder apparatus with thickness exaggerated for purposes of clarity and with the metal cover removed; and FIG. 4 is an enlarged top view of the holder apparatus.

DETAILED DESCRIPTION OF A PREFERRED EMBODIMENT

Referring initially to FIG. 1, a specimen slide 10 mounts a very thin section of tissue 11, which as shown can be a longitudinal section of an entire infant mouse. The slide 10 includes a rectangular piece of glass 12 having the tissue section 11 mounted thereon and covered by a thin coverslip layer 13 which extends up to a level 14. The region 15 above the level 14 provides space to adhere an identification sticker, and for handling the slide with the fingers. The tissue sample 11 can be most anything of interest to a diagnostician or clinician, and can be relatively large in size. For example, the entire section of a human gonad gland, ovary, artery or vein can be readily mounted in the slide 10. The slide 10 fits into a holder 20 that is constructed in accordance with the present invention. The structural details of the holder 20 will be described below. The holder 20 is sized and arranged to be received in the receptacle 21 of a 35 mm photographic slide scanner 22 that contains a charge-coupled scanning array of sensors that allows the entire viewing area of a 36 mm×24 mm color slide to be scanned at 2700 dpi in approximately one (1) minute. The scanner 22 is commercially available as the "SprintScan" 35 scanner from Polaroid Corp. Electrical signals from the scanner 22 are fed by a cable to a computer 23 and displayed on its monitor 24. A color print can be made on a printer (not shown) if desired.

The holder 20 is generally rectangular in shape and has elongated side walls 26, 27 and relatively shorter top and bottom walls 28, 30. A rectangular viewing window 31 is formed through the body 19 or the holder 20, and a slide receiving slot or pocket 35 that is formed within the body extends through an opening 34 in the top wall 28 and down past the lower edge 35 of the window 31. Although numerous materials could be used to make the body 19 of the holder 20, one preferred construction employs polished aluminum. The front wall of the body 19 can be recessed to a shallow depth except along a portion of each side as shown, and a thin metal cover plate 32 that is attached by screws or the like (not shown) and to close the front of the body. A rectangular window 31 is formed on the cover plate 32. A corresponding window 31' (FIG. 3) is formed through the back wall of the body 19.

As shown in more detail in FIG. 2, the edges 36, 37 which define the sides of the slot 35 are recessed to a slightly wider and deeper dimension in order to receive and retain a rectangular glass filter 40. The filter 40 is carefully made to be optically flat and clear so as not to introduce any distortion or aberration in color, and to have a neutral density so that the Kelvin temperature of light passing therethrough is not affected. The filter 40 does, however, reduce the amount of light passing through by about 40%.

The thin metal plate 32 when mounted on the body 19, traps the side edges of the filter 40 in the recessed edges 36 and 37 of the slot 35. When the specimen slide 10 is inserted through the opening 34 and advanced fully downward in the slot 35 until its lower end surface rests on bottom wall 41, the sample 11 will appear in the window 31 while the top portion 15 extends well above tile top wall 28 so that it can be grasped by the fingers for insertion and removal. FIG. 3 is a fragmentary cross-section which shows the slide assembly 10 positioned in the slot 35 with specimen sandwiched between the glass 12 and the thin piece of coverslip 13 and positioned in tile window 31. A suitable light source such as a florescent device 50 which puts out daylight white light at a Kelvin temperature of about 5600# shines through the filter glass 40 and illuminates the specimen in the slide 10.

The CCD array 51 in the scanner 22 scans the entire area of the window 31 at a resolution of 2700×1800 dpi and produces signals which are fed directly to the hard drive of the computer 23. A very high resolution color image of the tissue sample 11 is obtained, and the sample size can be as large as 35 mm×24 mm.

OPERATION

In operation and use, a thin slice or section of tissue 11 is mounted on the glass 12 of the slide 10, and the section is covered by the coverslip 13. Then the slide 10 is positioned in the holder 20 by inserting it down into the slot or pocket 35. When properly positioned, the tissue 11 is framed by the window 31 while the top portion 15 remains above the upper wall surface 28. The holder 20, which has approximately the same width and thickness dimensions as a 35 mm photographic slide, then is positioned in the receptacle 21 of the scanner 22 with the filter 40 on the outer side, or toward the light source 50 in the scanner. Light from the florescent source 50 passes through the window 31, the filter glass 40, the slide glass 12 and the window 31' and illuminates the section 11 which is scanned by the CCD array 51 to create a high resolution color image thereof. Due to the large size of the windows 31 and 31', the image scanned can be as large as 36 mm×24 mm, which allows the imaging of entire brain sections of certain research animals, human prostate and other glands, arteries, or any other microscopically large tissue section in a quick and economical manner. The system of the present invention eliminates the need for a low power microscope-video camera imaging system, and provides savings of thousands of dollars to an individual user.

Although the holder apparatus 20 has been described in connection with the orientation shown in the drawings, that is with the top thereof providing the opening into the slot 35, it will be recognized that the holder could be loaded in another type of scanner in an orientation other than the vertical, or into the side of the scanner 22 in another orientation. Thus the use herein of phrases such as "top", and "bottom" are merely for purposes of convenience of illustration, and not in any limitative sense. It also is within the scope of the present invention for the holder apparatus 20 to already be positioned in the receptacle 20 when the slide 10 is inserted therein.

It now will be recognized that a new and improved system for providing a high resolution color image of a large tissue sample has been disclosed. Since certain changes or modifications may be made in the disclosed embodiment without departing from the inventive concepts involved, it is the aim of the appended claims to cover all such changes and notifications falling within the true spirit and scope of the present invention.

What is claimed is:

1. A system for use in obtaining a high resolution color image of a large tissue sample mounted in a microscope specimen slide, comprising: scanner means having a receptacle sized and arranged to receive a photographic slide of standard dimensions, said scanner means having a light source and sensor means for scanning a slide and providing a high resolution color image thereof; and holder means sized and arranged to be received in said receptacle and to mount said microscope specimen slide, said holder means defining an elongated slot into which said microscope specimen slide is inserted and a window that is opposite said tissue sample when said slide is positioned in said slot, an optically flat, clear, neutral density filter mounted in said window and coveting the same to reduce the amount of light illuminating said tissue sample, said sensor means providing output signals representative of said image, and means for transmitting said signals to a computer.

2. A system for use in obtaining a high resolution color image of a large tissue sample mounted in a microscope specimen slide, comprising: scanner means having a receptacle sized and arranged to receive a photographic slide of standard dimensions, said scanner means having a light source and sensor means for scanning a slide and providing a high resolution color image thereof; and holder means sized and arranged to be received in said receptacle and to mount said microscope specimen slide, said holder means defining an elongated slot into which said microscope specimen slide is inserted and a window that is opposite said tissue sample when said microscopic specimen slide is positioned in said slot, and an optically flat, clear, neutral density glass filter mounted in said window and covering the same to reduce the amount of light illuminating said tissue sample without reducing the Kelvin temperature thereof, said sensor means providing output signals representative of said image, and further including means for transmitting said signals to the hard drive of a computer.

3. The system of claim 2 which said scanner means has a resolution as high as 2700×1800 dots per inch.

4. A holder apparatus for use in enabling a microscope glass specimen slide to be positioned in a photographic slide scanner, said scanner having a slide-receiving receptacle, comprising: generally rectangular housing means sized and arranged to be received in said receptacle, said housing means having front and rear wall surfaces and opposite end wall surfaces; front and rear window means opening through said respective front and rear wall surfaces; generally rectangular slot means formed in said housing means and opening through one of said end wall surfaces and being sized and arranged to receive said microscope glass specimen slide in a manner such that a large tissue sample mounted therein is located adjacent said front and rear window means; and glass filter means covering one of said window means, said glass filter means being sized and arranged to be positioned between said glass specimen slide and a light source that is used to illuminate said tissue sample.

5. The holder apparatus of claim 4 where said slide has a length that is greater than the depth of said slot means whereby an end portion of said slide extends beyond said slot means.

6. The holder apparatus of claim 4 wherein said glass filter means is optically flat and has a neutral density so as to reduce the amount of light impinging on said tissue sample without reducing the Kelvin temperature of such light.

7. The holder apparatus of claim 4 wherein said glass specimen slide has a length of three inches and a width of one inch, and said photographic slide scanner is a 35 mm photographic slide scanner.

8. A system for use in obtaining a high resolution color image of a large tissue sample mounted in a microscope specimen slide and comprising: scanner means having a receptacle sized and arranged to receive said microscope specimen slide, said scanner means having a light source and sensor means for scanning said microscope specimen slide to provide a high resolution image thereof; holder means sized and arranged to be received in said receptacle and to mount said microscope specimen slide, said holder means defining slide retainer means into which said microscope specimen slide is inserted and a window that is opposite said tissue sample when said slide is positioned in said slide retainer means, said sensor means providing output signals representative of said image, and means for transmitting said signals to a computer.

9. The system of claim 8 wherein a filter is mounted over said window to reduce the amount of light illuminating said tissue sample.

10. The system of claim 8 wherein a monitor is associated with said computer for display of information concerning said tissue sample.

* * * * *

UNITED STATES PATENT AND TRADEMARK OFFICE
Certificate

Patent No. 5,612,819                                              Patented: March 18, 1997

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Robert D. Meyer, Houston, Texas; and Matthew McMahon Batchelor, Orange, Texas.

Signed and Sealed this First Day of February, 2000.

TIMOTHY P. CALLAHAN
*Supervisory Patent Examiner*
Art Unit 2816